United States Patent
Lin et al.

(10) Patent No.: US 11,524,044 B2
(45) Date of Patent: Dec. 13, 2022

(54) STRENGTHENING AND TUMOR ELIMINATING TRADITIONAL CHINESE MEDICINE COMPOSITION, ITS PREPARATION METHOD AND APPLICATION

(71) Applicant: The First Afiliated Hospital Of Guangzhou University Of Chinese Medicine, Guangzhou (CN)

(72) Inventors: Lizhu Lin, Guangzhou (CN); Hongmei Tang, Guangzhou (CN); Jianfeng Gan, Guangzhou (CN); Detang Li, Foshan (CN); Lingling Sun, Guangzhou (CN)

(73) Assignee: The First Afiliated Hospital of Guangzhou University of Chinese Medicine, Guangzhou (CN)

( * ) Notice: Subject to any disclaimer, the term of this patent is extended or adjusted under 35 U.S.C. 154(b) by 202 days.

(21) Appl. No.: 17/151,923

(22) Filed: Jan. 19, 2021

(65) Prior Publication Data

US 2022/0152143 A1    May 19, 2022

(30) Foreign Application Priority Data

Nov. 17, 2020  (CN) .......................... 202011285356.6

(51) Int. Cl.
| | | |
|---|---|---|
| *A61K 36/898* | (2006.01) | |
| *A61P 35/00* | (2006.01) | |
| *A61K 9/16* | (2006.01) | |
| *A61K 36/076* | (2006.01) | |
| *A61K 36/18* | (2006.01) | |
| *A61K 36/28* | (2006.01) | |
| *A61K 36/284* | (2006.01) | |
| *A61K 36/344* | (2006.01) | |
| *A61K 36/484* | (2006.01) | |
| *A61K 36/539* | (2006.01) | |
| *A61K 36/638* | (2006.01) | |
| *A61K 36/736* | (2006.01) | |

(52) U.S. Cl.
CPC .......... *A61K 36/898* (2013.01); *A61K 9/1694* (2013.01); *A61K 36/076* (2013.01); *A61K 36/18* (2013.01); *A61K 36/28* (2013.01); *A61K 36/284* (2013.01); *A61K 36/344* (2013.01); *A61K 36/484* (2013.01); *A61K 36/539* (2013.01); *A61K 36/638* (2013.01); *A61K 36/736* (2013.01); *A61P 35/00* (2018.01); *A61K 2236/31* (2013.01); *A61K 2236/331* (2013.01); *A61K 2236/51* (2013.01); *A61K 2236/53* (2013.01)

(58) Field of Classification Search
None
See application file for complete search history.

(56) References Cited

FOREIGN PATENT DOCUMENTS

CN    113730535 A  * 12/2021

* cited by examiner

*Primary Examiner* — Aaron J Kosar
(74) *Attorney, Agent, or Firm* — Schmeiser, Olsen & Watts LLP

(57) ABSTRACT

This invention provides a strengthening and tumor eliminating traditional Chinese medicine composition, its preparation method and application, which specifically relate to the technical field of the treatment of intermediate and advanced stage and postoperative malignant tumor, wherein the strengthening and tumor eliminating traditional Chinese medicine composition comprises: 8-30 parts of *Radix codonopsis*, 5-30 parts of *Rhizoma atractylodis* Macrocephalae, 5-30 parts of *Poria cocos*, 5-30 parts of Pseudobulb of *Appendiculate cremastra*, 5-30 parts of *Scutellaria barbata*, 5-30 parts of *Sarcandra glabra*, 3-30 parts of peach kernel, 2-30 parts of *Ligustrum lucidum*, 5-30 parts of *Eclipta* and 1-20 parts of licorice. This invention also provides a preparation method of the described strengthening and tumor eliminating traditional Chinese medicine composition.

10 Claims, No Drawings

STRENGTHENING AND TUMOR ELIMINATING TRADITIONAL CHINESE MEDICINE COMPOSITION, ITS PREPARATION METHOD AND APPLICATION

TECHNICAL FIELD

This invention relates to the technical field of the treatment of intermediate and advanced stage and postoperative malignant tumor, in particular to a strengthening and tumor eliminating traditional Chinese medicine composition, its preparation method and application.

BACKGROUND TECHNOLOGY

Tumor includes benign tumor and malignant tumor, while cancer generally refers to malignant tumor. The malignant tumor from epithelial tissue is called cancer, and the malignant tumor from mesenchymal tissue is called sarcoma; the former is easily metastasized through lymph nodes, while the latter mostly spreads through blood circulation. From the perspective of world share, China has a high proportion of cancer patients, and cancer has become one of the main causes of death in China, which has caused a huge and heavy burden on China's social economy. At present, the main treatments of cancer include medical treatment, surgical treatment, radiation therapy and so on. The treatments of modern medicine have the characteristics of attaching importance to the local control of tumor, having strong killing power to the tumor cells of cancer and being able to better control the local tumor body. However, they neglect the function adjustment of the whole body, which is easy to lead to over treatment of cancer. As a result, the body function of patients is often damaged and the quality of life is reduced; in addition, intermediate and advanced stage cancer patients lack of surgical indications, and radiotherapy, chemotherapy and targeted therapy do great harm to the physical condition of patients.

Chinese medicine also has some understanding of tumor. According to *The Yellow Emperors Internal Classic*, the earliest medical classic in China, tumor is caused by "obstructed circulation of nutrient Qi and defensive Qi", "cold Qi stays outside the intestine and fights with defensive Qi" and "pathogenic Qi stays among it". Traditional Chinese medicine still has a unique position and role in modern oncology. The treatment of malignant tumor with traditional Chinese medicine has three characteristics: effectiveness, diversity and persistence, which are reflected in the individualization of syndrome differentiation and treatment; multiple active ingredients and multiple target functioning; eliminating pathogenic factors without hurting the body and strengthening the body without leaving pathogenic factors; lasting curative effect; being non-toxic or low toxic; being suitable for long-term treatment. Western medicine has a good effect in killing tumor cells, controlling local tumor body and cancer pain; traditional Chinese medicine can develop prescriptions and apply medicines based on syndrome differentiation and treatment with less adverse reactions, which can reduce the symptoms of patients, so that the patients in advanced stage who cannot treated by western medicine can achieve "survival with tumor", and can also reduce the adverse reactions caused by western medicine treatment; the combination of traditional Chinese medicine and Western medicine, the combination of external and internal therapy, the combination of strengthening the body and eliminating pathogenic factors, and the better treatment of cancer, is the research field of the treatment of intermediate and advanced stage and postoperative malignant tumor.

SUMMARY OF THE INVENTION

The purpose of this invention is to solve all kinds of drawbacks in the above treatments of western medicine, and provide a strengthening and tumor eliminating traditional Chinese medicine composition, which combines the external and internal therapy and combines strengthening the body and eliminating pathogenic factors through the research of traditional Chinese medicine. This strengthening and tumor eliminating traditional Chinese medicine composition has the effects of spleen strengthening, qi replenishing, anti-tumor and lump dissolving. It is used in spleen deficiency and phlegm-stasis type intermediate and advanced stage and postoperative tumor, and the symptoms are fatigue, phlegm nodule aggregation.

To achieve the above purpose, this invention provides the following scheme:

This invention provides a strengthening and tumor eliminating traditional Chinese medicine composition, which comprises components of the following pbw: 8-30 parts of *Radix codonopsis*, 5-30 parts of *Rhizoma atractylodis* Macrocephalae, 5-30 parts of *Poria cocos*, 5-30 parts of Pseudobulb of *Appendiculate cremastra*, 5-30 parts of *Scutellaria barbata*, 5-30 parts of *Sarcandra glabra*, 3-30 parts of peach kernel, 2-30 parts of *Ligustrum lucidum*, 5-30 parts of *Eclipta* and 1-20 parts of licorice.

The strengthening and tumor eliminating traditional Chinese medicine composition described in a further optimization of this invention comprises components of the following pbw: 8-12 parts of *Radix codonopsis*, 12-18 parts of *Rhizoma atractylodis* Macrocephalae, 8-12 parts of *Poria cocos*, 7-11 parts of Pseudobulb of *Appendiculate cremastra*, 8-12 parts of *Scutellaria barbata*, 8-12 parts of *Sarcandra glabra*, 4-7 parts of peach kernel, 8-12 parts of *Ligustrum lucidum*, 8-12 parts of *Eclipta* and 2-5 parts of licorice.

As a further optimization of the invention, the strengthening and tumor eliminating traditional Chinese medicine composition described in a further optimization of this invention comprises components of the following pbw: 10 parts of *Radix codonopsis*, 15 parts of *Rhizoma atractylodis* Macrocephalae, 10 parts of *Poria cocos*, 9 parts of Pseudobulb of *Appendiculate cremastra*, 10 parts of *Scutellaria barbata*, 10 parts of *Sarcandra glabra*, 5 parts of peach kernel, 10 parts of *Ligustrum lucidum*, 10 parts of *Eclipta* and 3 parts of licorice.

This invention also provides a method for preparing the strengthening and tumor eliminating traditional Chinese medicine composition, which comprises the following steps:

(1) Weigh the raw materials with corresponding pbw;

(2) Mix the raw materials weighed in step (1), decoct them with an appropriate amount of water to obtain the decoction, and filter the decoction to obtain the filtrate;

(3) Concentrate the filtrate obtained in step (2) under vacuum to make the extract with relative density of 1.20-1.25 at 60° C., dry the extract in vacuum, crush it to make the dry extract powder, and obtain the strengthening and tumor eliminating traditional Chinese medicine composition.

As a further optimization of this invention, the described step (2) is to mix the raw materials weighed in step (1) and decoct them one or more times. Add water 10 times the amount of the raw materials and decoct them for 1.5 h each time. After each decocting, filter it through a 200 mesh sieve to get the filtrate and dregs, and merge the filtrate.

As a further optimization of this invention, the vacuum drying conditions in the described step (3) are as follows: the thickness of the paving material is controlled to be 0.7-1.0 cm, the drying temperature is 60-80° C., and the vacuum degree is −0.08 Mpa to −0.10 Mpa.

This invention also provides the application of the described strengthening and tumor eliminating traditional Chinese medicine composition for preparing cancer drug.

As a further optimization of this invention, the described cancer drug comprises the strengthening and tumor eliminating traditional Chinese medicine composition and pharmaceutically acceptable excipients or auxiliary components, which can be processed into any dosage form suitable for pharmaceutical use.

As a further optimization of this invention, the dosage forms of the described cancer drug are decoction, pill, capsule, tablet or granule.

As a further optimization of this invention, the preparation method of granules of the described cancer drug is as follows: add the pharmaceutically acceptable excipients or auxiliary components into the described dry extract powder, mix it well, wet granulate, add 90% ethanol to make soft material, granulate, dry it until the moisture content of the granules is ≤6%, arrange granules, and check the appearance, granularity and solubility of the semi-finished granules to obtain the granules of the strengthening and tumor eliminating traditional Chinese medicine composition, in which the content of the dry extract powder is 45%.

As a further optimization of this invention, the described cancer is a kind of spleen deficiency and phlegm-stasis type intermediate and advanced stage and postoperative malignant tumor.

The pharmacological description of the raw material components in this invention is as follows:

*Radix codonopsis*: it tastes sweet and is neutral in nature. Its channel tropism is lung and spleen. It has the effect of Qi replenishing, stomach, spleen, and lung strengthening. In this invention, it plays the role of spleen strengthening and Qi replenishing, and is a "Monarch" medicine. Its chemical compositions mainly include polysaccharides, glycosides, steroids, amino acids, alkaloids and so on. *Radix codonopsis* has the functions of anti-ulcer, protecting gastric mucosa, regulating gastrointestinal motility, promoting hematopoiesis and regulating blood pressure.

*Rhizoma atractylodis* Macrocephalae: it has the effect of strengthening, Qi replenishing, eliminating dampness, dieresis relieving, antiperspiration and miscarriage prevention. In this invention, it plays the role of spleen strengthening and Qi replenishing, and is a "Monarch" medicine. It mainly contains water-soluble polysaccharide. The polysaccharide of *Rhizoma atractylodis* Macrocephalae can produce specific IgG type and non-specific cross antibodies; *Rhizoma atractylodis* Macrocephalae has the function of promoting the proliferation of the probiotics, that is, *Bifidobacterium* and lactic acid bacteria, in intestinal flora and improving the status of intestinal flora.

*Poria cocos*: it has the functions of excreting dampness, dieresis relieving, stomach soothing, spleen strengthening, mind calming, bacteriostasis, enhancing the body's disease resistance and reducing blood sugar. In this invention, it plays the role of spleen strengthening and Qi replenishing, and is a "Monarch" medicine. Its main chemical composition is pachyman with a content of about 84.2%, including β-pachyman, glucose, sucrose and fructose. Pachyman has the function of enhancing immune function. It has the function of anti-thymus atrophy, anti-spleen enlargement and anti-tumor growth. In addition, *Poria cocos* also contains ergosterol, poriatin, hard alkane, cellulose, triterpenoids, octanoic acid, lauric acid, dodecanoic acid, histidine, choline, protein, fat, enzyme, adenine, gum and other components, in which choline can enhance and improve brain function. Poriatin is a group of small molecule tetracyclic triterpenoids, which exist in plants in the form of acids.

Pseudobulb of *Appendiculate cremastra*: it has the effect of clearing away heat and toxin, swelling dispersing and lump dissolving. In this invention, it plays the role of anti-tumor and lump dissolving, and is a "Minister" medicine. The main chemical compositions include dihydrophenanthrene and bibenzyl compounds. Cirrhopetalanthrin, a chemical component of Pseudobulb of *Appendiculate cremastra*, showed moderate cytotoxicity on human colon cancer, liver cancer, gastric cancer, lung cancer and breast cancer related cells, indicating that Pseudobulb of *Appendiculate cremastra* has certain antitumor activity.

*Scutellaria barbata*: it has the effect of clearing away heat and toxin, dissipating blood stasis and stopping bleeding, dieresis relieving and swelling dispersing. In this invention, it plays the role of anti-tumor and lump dissolving, and is a "Minister" medicine. *Scutellaria barbata* mainly contains flavonoids, diterpenes, lipids and polysaccharides. In this invention, *Scutellaria barbata* is applied in the treatment of tumor in combination with other drugs, which has a remarkable effect.

*Sarcandra glabra*: it has the effect of antibacterial and anti-inflammatory, wind expelling and circulation tract unblocking, blood circulation invigorating and lump dissolving. In this invention, it plays the role of anti-tumor and lump dissolving, and is a "Minister" medicine. Its main chemical compositions include sesquiterpenoids, flavonoids, coumarins and organic acids.

Peach kernel: it has the effect of invigorating blood circulation and dissipating blood stasis, and relaxing bowel. In this invention, it plays the role of anti-tumor and lump dissolving, and is a "Minister" medicine. Its main chemical compositions include lipids (neutral lipids, glycolipids, phospholipids), glycosides (amygdalin, Prunasin), sugars and proteins. Peach kernel can intervene the development of mature plaque in ApoE deficient mice, and has a certain effect on stabilizing plaque. Its mechanism may be related to regulating lipid metabolism and inhibiting inflammation; water extract of peach kernel, amygdalin and fatty oil of peach kernel all inhibit ADP induced platelet aggregation in varying degrees.

*Ligustrum lucidum*: it has the effect of nourishing liver and kidney, improving eyesight and darkening hair. It is used for Yin deficiency of liver and kidney, dizziness and tinnitus, soreness and weakness of waist and knee, premature graying hair, dim vision, internal heat dispersion-thirst and hectic fever. In this invention, it plays the role of nourishing liver and kidney, and is an "Assistant" medicine. Its main active compositions include polysaccharides, flavonoids, iridoids and triterpenoids, wherein triterpenoids include ursanes, oleananes, dammaranes and lupanes.

*Eclipta*: it has the effect of nourishing Yin and kidney, cooling blood and stopping bleeding. In this invention, it plays the role of nourishing liver and kidney, and is an "Assistant" medicine. Its main chemical compositions have triterpenoids, flavonoids, coumarins and steroids. *Eclipta* has strong pharmacological actions such as immunoregulation, liver protection, anti-fibrosis, anti-tumor, anti-free radical, anti-oxidation and enzyme activation.

Licorice: it has the effect of strengthening spleen and Qi, moistening lung and relieving cough, relieving pain and drug effect, which is a "Guide" medicine. In this invention, it plays the role of strengthening spleen and stomach. Its main chemical compositions include glycyrrhizic acid, glycyrrhetinic acid, flavonoids, polysaccharides and so on. Flavonoids of *Glycyrrhiza* can inhibit the atrophy of gastric mucosa glands in rats with chronic atrophic gastritis.

This invention discloses the following technical effects:

The strengthening and tumor eliminating traditional Chinese medicine composition of this invention has the effects of spleen strengthening, qi replenishing, anti-tumor and lump dissolving. In this prescription, the "Monarch" medicines are *Radix codonopsis, Rhizoma atractylodis* Macrocephalae and *Poria cocos*, which play the role of spleen strengthening and qi replenishing; the "Minister" medicines are Pseudobulb of *Appendiculate cremastra, Scutellaria barbata, Sarcandra glabra* and peach kernel, which play the role of anti-tumor and lump dissolving; the "Assistant" medicines are *Ligustrum lucidum* and *Eclipta*, which play the role of nourishing liver and kidney; the "Guide" medicine is licorice, which play the role of harmonizing other medicines, strengthening spleen and stomach. Through the synergistic effect among the components of the traditional Chinese medicine of this invention, the composition is used for the clinical treatment of spleen deficiency and phlegm-stasis type intermediate and advanced stage and postoperative tumor of the patients with symptoms such as fatigue and phlegm nodule aggregation. It is safe and effective in clinical use.

The strengthening and tumor eliminating granule in this invention has the advantages of large drug loading amount, good stability, easy taking and carrying, etc. It is not only suitable for patients to take for a long time, but also can meet the needs of clinical medication and preparation production.

DESCRIPTION OF THE INVENTION

Various exemplary embodiments of this invention will be described in detail, which should not be considered as a limitation of this invention, but as a more detailed description of certain aspects, characteristics and embodiments of this invention.

It should be understood that the terms used in this invention are only for describing particular embodiments and are not intended to limit this invention. In addition, for the numerical range in this invention, it should be understood that each intermediate value between the upper and lower limits of the range is also specifically disclosed. Each smaller range between any stated value or the intermediate value within the stated range and any other stated value or the intermediate value within the described range is also included in this invention. The upper and lower limits of these smaller ranges can be included or excluded from the range independently.

Unless otherwise indicated, all technical and scientific terms used herein have the same meaning commonly understood by those of ordinary skill in the art of this invention. Although this invention only describes preferred methods and materials, any methods and materials similar to or equivalent to those described herein may also be used in the embodiments or tests of this invention. All documents in these instructions are incorporated by reference to disclose and describe the methods and/or materials related to the described documents. In case of conflict with any incorporated document, the content of these instructions shall prevail.

Without deviating from the scope or spirit of this invention, various improvements and changes can be made to the specific embodiments of the instructions of this invention, which is obvious to those skilled in the art. Other embodiments obtained from the instructions of this invention are obvious to the technicians. The instructions and embodiments of this application are exemplary only.

The words "contain", "include", "possess", "have" and so on used in this paper are all open terms, that is, they mean to include but not limited to.

Embodiment 1

(1) Weigh 10 parts of *Radix codonopsis*, 15 parts of *Rhizoma atractylodis* Macrocephalae, 10 parts of *Poria cocos*, 9 parts of Pseudobulb of *Appendiculate cremastra*, 10 parts of *Scutellaria barbata*, 10 parts of *Sarcandra glabra*, 5 parts of peach kernel, 10 parts of *Ligustrum lucidum*, 10 parts of *Eclipta* and 3 parts of licorice.

(2) Mix the weighed medicinal materials, add 10 times of water, decoct for 1.5 h, and filter it with a 200 mesh sieve while it is hot to get the filtrate and dregs. Again, add 10 times of water to the dregs, decoct for 1.5 h, and filter it with a 200 mesh sieve while it is hot to get the filtrate and dregs. Merge the above two filtrate.

(3) Concentrate the filtrate obtained in step (2) to an extract with a relative density of 1.20 (60° C.). Take the extract. The thickness of the paving material is controlled to be 1.0 cm, the drying temperature is 60° C., and the vacuum degree is −0.09 Mpa. Vacuum dry and crush it, and filter it with an 80 mesh sieve to the dry extract powder.

(4) Take appropriate amount of dry extract powder and dextrin, mix well, and granulate by wet method. Add 90% medicinal softwood made with ethanol, filter it with a 14 mesh sieve and granulate, dry it at 70° C. until the moisture content of the granules ≤6%, and filter the whole granules with a 12 mesh sieve, Check the appearance, granularity and solubility of the semi-finished granules to obtain the granules of the strengthening and tumor eliminating traditional Chinese medicine composition. The content of dry extract powder is 45%.

Embodiment 2

(1) Weigh 8 parts of *Radix codonopsis*, 18 parts of *Rhizoma atractylodis* Macrocephalae, 10 parts of *Poria cocos*, 7 parts of Pseudobulb of *Appendiculate cremastra*, 10 parts of *Scutellaria barbata*, 12 parts of *Sarcandra glabra*, 4 parts of peach kernel, 8 parts of *Ligustrum lucidum*, 10 parts of *Eclipta* and 5 parts of licorice.

(2) Mix the weighed medicinal materials, add 10 times of water, decoct for 1.5 h, and filter it with a 200 mesh sieve while it is hot to get the filtrate and dregs. Again, add 10 times of water to the dregs, decoct for 1.5 h, and filter it with a 200 mesh sieve while it is hot to get the filtrate and dregs. Merge the above two filtrate.

(3) Concentrate the filtrate obtained in step (2) to an extract with a relative density of 1.23 (60° C.). Take the extract. The thickness of the paving material is controlled to be 0.8 cm, the drying temperature is 70° C., and the vacuum degree is −0.10 Mpa. Vacuum dry and crush it, and filter it with an 80 mesh sieve to the dry extract powder.

(4) Take appropriate amount of dry extract powder and dextrin, mix well, and granulate by wet method. Add 90% medicinal softwood made with ethanol, filter it with a 14 mesh sieve and granulate, dry it at 60° C. until the moisture content of the granules ≤6%, and filter the whole granules with a 12 mesh sieve, Check the appearance, granularity and solubility of the semi-finished granules to obtain the granules of the strengthening and tumor eliminating traditional Chinese medicine composition. The content of dry extract powder is 45%.

Embodiment 3

(1) Weigh 12 parts of *Radix codonopsis,* 18 parts of *Rhizoma atractylodis* Macrocephalae, 12 parts of *Poria cocos,* 10 parts of Pseudobulb of *Appendiculate cremastra,* 12 parts of *Scutellaria barbata,* 8 parts of *Sarcandra glabra,* 6 parts of peach kernel, 12 parts of *Ligustrum lucidum,* 8 parts of *Eclipta* and 2 parts of licorice.

(2) Mix the weighed medicinal materials, add 10 times of water, decoct for 1.5 h, and filter it with a 200 mesh sieve while it is hot to get the filtrate and dregs. Again, add 10 times of water to the dregs, decoct for 1.5 h, and filter it with a 200 mesh sieve while it is hot to get the filtrate and dregs. Merge the above two filtrate.

(3) Concentrate the filtrate obtained in step (2) to an extract with a relative density of 1.25 (60° C.). Take the extract. The thickness of the paving material is controlled to be 0.7 cm, the drying temperature is 70° C., and the vacuum degree is −0.09 Mpa. Vacuum dry and crush it, and filter it with an 80 mesh sieve to the dry extract powder.

(4) Take appropriate amount of dry extract powder and dextrin, mix well, and granulate by wet method. Add 90% medicinal softwood made with ethanol, filter it with a 14 mesh sieve and granulate, dry it at 65° C. until the moisture content of the granules ≤6%, and filter the whole granules with a 12 mesh sieve, Check the appearance, granularity and solubility of the semi-finished granules to obtain the granules of the strengthening and tumor eliminating traditional Chinese medicine composition. The content of dry extract powder is 45%.

Embodiment 4

(1) Weigh 10 parts of *Radix codonopsis,* 12 parts of *Rhizoma atractylodis* Macrocephalae, 8 parts of *Poria cocos,* 11 parts of Pseudobulb of *Appendiculate cremastra,* 8 parts of *Scutellaria barbata,* 11 parts of *Sarcandra glabra,* 7 parts of peach kernel, 12 parts of *Ligustrum lucidum,* 12 parts of *Eclipta* and 4 parts of licorice.

(2) Mix the weighed medicinal materials, add 10 times of water, decoct for 1.5 h, and filter it with a 200 mesh sieve while it is hot to get the filtrate and dregs. Again, add 10 times of water to the dregs, decoct for 1.5 h, and filter it with a 200 mesh sieve while it is hot to get the filtrate and dregs. Merge the above two filtrate.

(3) Concentrate the filtrate obtained in step (2) to an extract with a relative density of 1.20 (60° C.). Take the extract. The thickness of the paving material is controlled to be 0.9 cm, the drying temperature is 80° C., and the vacuum degree is −0.08 Mpa. Vacuum dry and crush it, and filter it with an 80 mesh sieve to the dry extract powder.

(4) Take appropriate amount of dry extract powder and dextrin, mix well, and granulate by wet method. Add 90% medicinal softwood made with ethanol, filter it with a 14 mesh sieve and granulate, dry it at 65° C. until the moisture content of the granules ≤6%, and filter the whole granules with a 12 mesh sieve, Check the appearance, granularity and solubility of the semi-finished granules to obtain the granules of the strengthening and tumor eliminating traditional Chinese medicine composition. The content of dry extract powder is 45%.

Embodiment 5

(1) Weigh 8 parts of *Radix codonopsis,* 5 parts of *Rhizoma atractylodis* Macrocephalae, 5 parts of *Poria cocos,* 5 parts of Pseudobulb of *Appendiculate cremastra,* 5 parts of *Scutellaria barbata,* 5 parts of *Sarcandra glabra,* 3 parts of peach kernel, 2 parts of *Ligustrum lucidum,* 5 parts of *Eclipta* and 1 part of licorice.

(2) Mix the weighed medicinal materials, add 10 times of water, decoct for 1.5 h, and filter it with a 200 mesh sieve while it is hot to get the filtrate and dregs. Again, add 10 times of water to the dregs, decoct for 1.5 h, and filter it with a 200 mesh sieve while it is hot to get the filtrate and dregs. Merge the above two filtrate.

(3) Concentrate the filtrate obtained in step (2) to an extract with a relative density of 1.20 (60° C.). Take the extract. The thickness of the paving material is controlled to be 1.0 cm, the drying temperature is 60° C., and the vacuum degree is −0.09 Mpa. Vacuum dry and crush it, and filter it with an 80 mesh sieve to the dry extract powder.

(4) Take appropriate amount of dry extract powder and dextrin, mix well, and granulate by wet method. Add 90% medicinal softwood made with ethanol, filter it with a 14 mesh sieve and granulate, dry it at 70° C. until the moisture content of the granules ≤6%, and filter the whole granules with a 12 mesh sieve, Check the appearance, granularity and solubility of the semi-finished granules to obtain the granules of the strengthening and tumor eliminating traditional Chinese medicine composition. The content of dry extract powder is 45%.

Embodiment 6

(1) Weigh 30 parts of *Radix codonopsis,* 28 parts of *Rhizoma atractylodis* Macrocephalae, 25 parts of *Poria cocos,* 30 parts of Pseudobulb of *Appendiculate cremastra,* 25 parts of *Scutellaria barbata,* 26 parts of *Sarcandra glabra,* 30 parts of peach kernel, 30 parts of *Ligustrum lucidum,* 28 parts of *Eclipta* and 19 parts of licorice.

(2) Mix the weighed medicinal materials, add 10 times of water, decoct for 1.5 h, and filter it with a 200 mesh sieve while it is hot to get the filtrate and dregs. Again, add 10 times of water to the dregs, decoct for 1.5 h, and filter it with a 200 mesh sieve while it is hot to get the filtrate and dregs. Merge the above two filtrate.

(3) Concentrate the filtrate obtained in step (2) to an extract with a relative density of 1.20 (60° C.). Take the extract. The thickness of the paving material is controlled to be 1.0 cm, the drying temperature is 60° C., and the vacuum degree is −0.09 Mpa. Vacuum dry and crush it, and filter it with an 80 mesh sieve to the dry extract powder.

(4) Take appropriate amount of dry extract powder and dextrin, mix well, and granulate by wet method. Add 90% medicinal softwood made with ethanol, filter it with a 14 mesh sieve and granulate, dry it at 70° C. until the moisture content of the granules ≤6%, and filter the whole granules with a 12 mesh sieve, Check the appearance, granularity and solubility of the semi-finished granules to obtain the granules of the strengthening and tumor eliminating traditional Chinese medicine composition. The content of dry extract powder is 45%.

Experimental Example 1

(1) Select 100 postoperative patients with lung cancer, each of whom took the granules of the strengthening and tumor eliminating traditional Chinese medicine composition prepared in Embodiments 1-6 every day. Take the granules with boiled water by 3 times a day and 2 bags at a time. After a long time of continuous follow-up observation of 100 patients, it was found that the strengthening and tumor eliminating therapy can delay the recurrence time after operation. The research results showed that the application of the strengthening and tumor eliminating therapy after operation could reduce the risk in disease progress by 80%. If adjuvant chemotherapy is completed <4 cycles, the long-term treatment (>6 months) of the strengthening and tumor eliminating composition can extend the disease-free survival for about 3 years. If the adjuvant chemotherapy is completed >4 cycles, benefit from the strengthening and tumor eliminating traditional Chinese medicine composition can last a longer period.

(2) Select 100 spleen deficiency and phlegm-stasis type intermediate and advanced stage patients with lung cancer, each of whom took the granules of the strengthening and tumor eliminating traditional Chinese medicine composition prepared in Embodiments 1-6 every day. Take the granules with boiled water by 3 times a day and 2 bags at a time. The strengthening and tumor eliminating traditional Chinese medicine composition was used on the basis of and in combination with chemotherapy for treatment. Through observation, it was found that it could reduce 40% of the risk of death and extend 5 months of the overall survival.

(3) The symptoms of spleen deficiency and phlegm-stasis type intermediate and advanced stage patients with liver cancer, and intestinal cancer include fatigue, anorexia and emaciation, cough, expectoration, and pain in chest, rib and back. Select 100 spleen deficiency and phlegm-stasis type intermediate and advanced stage patients with liver cancer or intestinal cancer respectively, each of whom took the granules of the strengthening and tumor eliminating traditional Chinese medicine composition prepared in Embodiments 1-6 every day. Take the granules with boiled water by 3 times a day and 2 bags at a time. The treatment with the strengthening and tumor eliminating traditional Chinese medicine composition can relieve cancer-related fatigue, increase weight, and relieve cough and expectoration and other symptoms of patients.

The embodiments described above describe the preferred modes of this invention only, not limit the scope of this invention. Without deviating from the design spirit of this invention, all modifications and improvements made by ordinary technicians in the art to the technical scheme of this invention shall fall into the protection scope determined by the claims of this invention.

The invention claimed is:

1. A strengthening and tumor eliminating traditional Chinese medicine composition, which is characterized in that the raw materials comprise components of the following in parts by weight of the composition (pbw) of: 8-30 parts of *Radix codonopsis;* 5-30 parts of *rhizoma Atractylodis Macrocephalae;* 5-30 parts of *Poria cocos;* 5-30 parts of pseudobulb of *Appendiculate cremastra;* 5-30 parts of *Scutellaria barbata;* 5-30 parts of *Sarcandra glabra;* 3-30 parts of peach kernel; 2-30 parts of *Ligustrum lucidum;* 5-30 parts of *Eclipta;* and 1-20 parts of licorice.

2. The strengthening and tumor eliminating traditional Chinese medicine composition according to claim 1, which is characterized in that it comprises components of the following pbw: 8-12 parts of *Radix codonopsis;* 12-18 parts of *Rhizoma atractylodis* macrocephalae; 8-12 parts of *Poria cocos;* 7-11 parts of pseudobulb of *Appendiculate cremastra;* 8-12 parts of *Scutellaria barbata;* 8-12 parts of *Sarcandra glabra;* 4-7 parts of peach kernel; 8-12 parts of *Ligustrum lucidum;* 8-12 parts of *Eclipta;* and 2-5 parts of licorice.

3. The strengthening and tumor eliminating traditional Chinese medicine composition according to claim 1, which is characterized in that it comprises components of the following pbw: 10 parts of *Radix codonopsis;* 15 parts of *Rhizoma atractylodis* macrocephalae; 10 parts of *Poria cocos;* 9 parts of pseudobulb of *Appendiculate cremastra;* 10 parts of *Scutellaria barbata;* 10 parts of *Sarcandra glabra;* 5 parts of peach kernel; 10 parts of *Ligustrum lucidum;* 10 parts of *Eclipta;* and 3 parts of licorice.

4. A composition comprising the strengthening and tumor eliminating traditional Chinese medicine composition, suitable for preparing a cancer drug, according to any one of claims 1 to 3.

5. The composition according to claim 4, characterized in that the cancer drug comprises the strengthening and tumor eliminating traditional Chinese medicine composition and pharmaceutically acceptable excipients or auxiliary components, which can be processed into a dosage form suitable for pharmaceutical use.

6. The composition according to claim 5, wherein the dosage form is a decoction, pill, capsule, tablet, or granule.

7. The composition according to claim 4, wherein the cancer is a spleen deficiency and phlegm-stasis type intermediate, an advanced stage, and/or postoperative malignant tumor.

8. A method for preparing the strengthening and tumor eliminating traditional Chinese medicine composition according to any one of claims 1 to 3, which is characterized in that it comprises the following steps:
   (i) weighing the raw materials;
   (ii) mixing the raw materials weighed in step (i), decocting the mixture with water to obtain a decoction, and filtering the decoction to obtain a filtrate; and
   (iii) concentrating the filtrate obtained in step (ii) under vacuum to make an extract with relative density of 1.20-1.25, drying the extract in vacuum, and crushing and sieving the dried extract to make a dry extract powder, and obtaining the strengthening and tumor eliminating traditional Chinese medicine composition.

9. The preparation method according to claim 8, which is characterized in that step (ii) comprises mixing the raw materials weighed in step (i) and decocting one or more times; adding water 10 times the amount of the raw materials and decocting for 1.5 hour each time; and after each decocting, filtering through a 200 mesh sieve to get a filtrate and dregs; and merging the filtrates.

10. The preparation method according to claim 8, which is characterized in that the vacuum drying conditions in step (iii) are as follows: providing a controlled thickness of the material of 0.7-1.0 cm, a drying temperature of 60-80° C., and a vacuum degree of −0.08 Mpa to −0.10 Mpa.

* * * * *